United States Patent
Echner

(10) Patent No.: US 9,437,339 B2
(45) Date of Patent: *Sep. 6, 2016

(54) LEAF ASSEMBLY FOR A MULTI-LEAF COLLIMATOR AND MULTI-LEAF COLLIMATOR

(71) Applicants: Deutsches Krebsforschungszentrum, Heidelberg (DE); Precisis AG, Heidelberg (DE)

(72) Inventor: Gernot Echner, Wiesenbach (DE)

(73) Assignees: Deutsches Krebsforschungszentrum, Heidelberg (DE); Precisis AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/415,086

(22) PCT Filed: Jul. 18, 2013

(86) PCT No.: PCT/EP2013/065170
§ 371 (c)(1),
(2) Date: Jan. 15, 2015

(87) PCT Pub. No.: WO2014/013009
PCT Pub. Date: Jan. 23, 2014

(65) Prior Publication Data
US 2015/0206613 A1    Jul. 23, 2015

(30) Foreign Application Priority Data

Jul. 19, 2012   (EP) .................................... 12177139

(51) Int. Cl.
G21K 5/04   (2006.01)
G21K 1/04   (2006.01)
A61N 5/10   (2006.01)

(52) U.S. Cl.
CPC ............. *G21K 1/046* (2013.01); *A61N 5/1045* (2013.01)

(58) Field of Classification Search
USPC .............. 250/396 R, 397, 398, 492.1, 492.3; 378/147, 150, 152; 600/1
See application file for complete search history.

(56) References Cited

U.S. PATENT DOCUMENTS

| 4,794,629 A | 12/1988 | Pastyr et al. |
| 5,351,280 A | 9/1994 | Swerdloff et al. |

(Continued)

FOREIGN PATENT DOCUMENTS

| EP | 2 090 333 | 10/2013 |
| WO | WO 2009/036813 A1 | 3/2009 |

OTHER PUBLICATIONS

International Search Report and Written Opinion issued in related International Patent Application No. PCT/EP2013/065170, completed Mar. 3, 2014.

(Continued)

*Primary Examiner* — Nicole Ippolito
(74) *Attorney, Agent, or Firm* — Foley & Lardner LLP

(57) ABSTRACT

The invention relates to a leaf assembly (102) for a multi-leaf collimator, comprising a leaf frame (104) and a plurality of leaves (106) for shielding beams (108) from a selected area, wherein the leaves (106) are arranged sideways and adjacently in the leaf frame (104) for shielding beams (108) being emitted from a radiation source (110) located above the assembly (102), wherein each leaf (106) is mounted in the leaf frame (104) displaceably in an adjusting direction (112) being oriented perpendicularly related to said beams (108), and wherein the leaf frame (104) provides a linear guidance (114) for each leaf (106) within the adjusting direction (112), being designed in a such a way that the leaf frame (104) is adapted to allow for lateral movement of the leaves (106) superposing said linear guidance (114), thus allowing mutual abutting of the leaves (106). Furthermore, the invention relates to a multi-leaf collimator comprising two leaf assemblies (102) according to the invention, wherein the assemblies (102) are arranged to face each other within the adjusting direction (112). The invention is based on the objective of designing a leaf assembly (102) for a multi-leaf collimator and a multi-leaf collimator in such a way that the occurrence of leak-age radiation may be diminished.

11 Claims, 6 Drawing Sheets

(56) References Cited

U.S. PATENT DOCUMENTS

Figure 1:
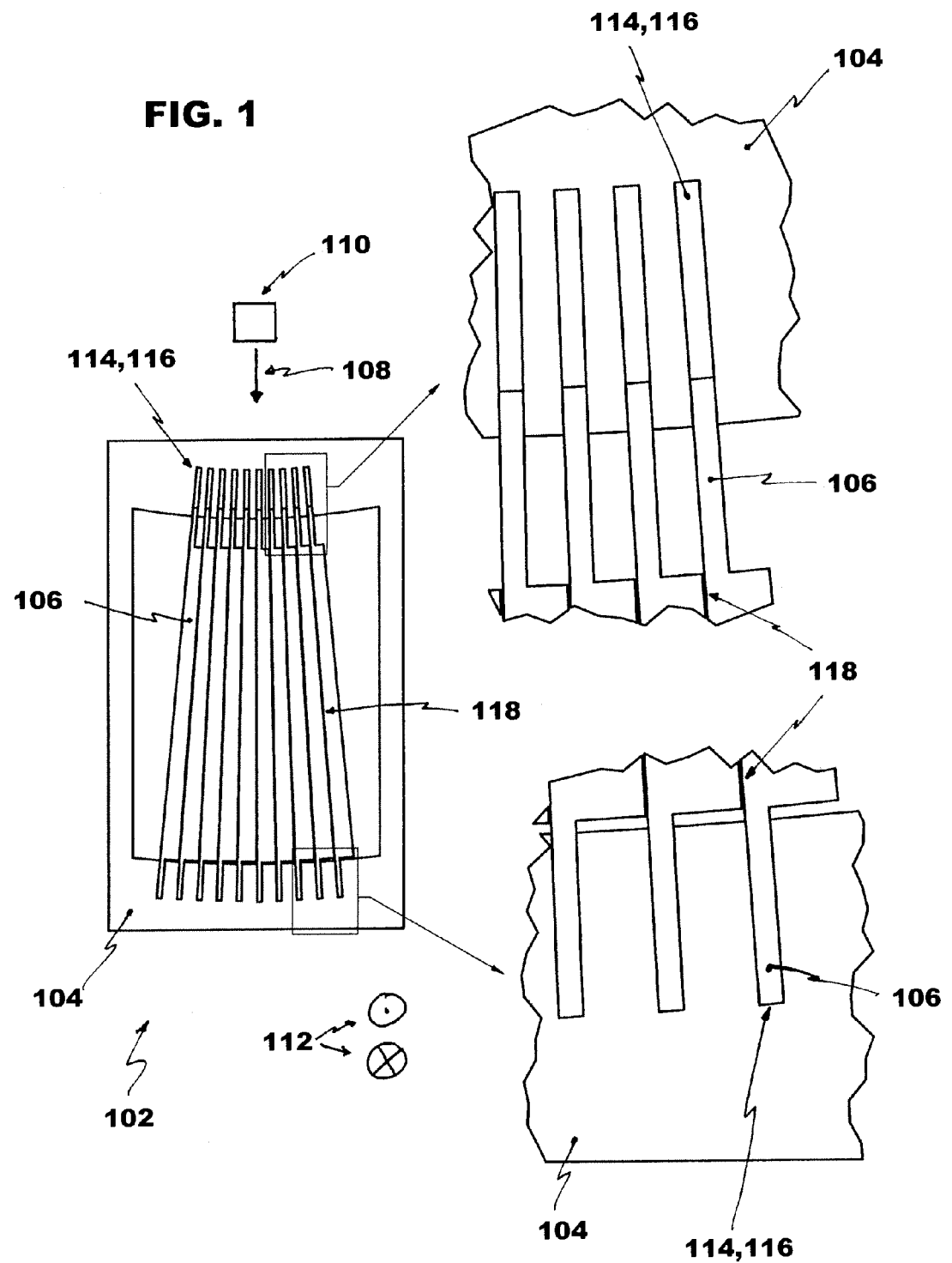

| | | |
|---|---|---|
| 5,668,371 A | 9/1997 | Deasy et al. |
| 2007/0164239 A1 | 7/2007 | Terwilliger et al. |
| 2009/0207975 A1* | 8/2009 | Bourne ............... A61N 5/1042 378/150 |
| 2012/0043482 A1 | 2/2012 | Prince et al. |

OTHER PUBLICATIONS

Hariri et al., "Suggesting a new design for multileaf collimator leaves based on Monte Carlo simulation of two commercial systems," J. of Appl. Clinical Medical Physics., vol. 11, No. 3, pp. 173-185 (2010).

Office Action issued in related U.S. Appl. No. 14/415,097, dated Sep. 29, 2015.

Office Action issued in related U.S. Appl. No. 14/415,097, dated Jan. 25, 2016.

Notice of Allowance issued in related U.S. Appl. No. 14/415,097, dated May 4, 2016.

* cited by examiner

LEAF ASSEMBLY FOR A MULTI-LEAF COLLIMATOR AND MULTI-LEAF COLLIMATOR

The invention relates to a leaf assembly for a multi-leaf collimator, comprising a leaf frame and a plurality of leaves for shielding beams from a selected area, wherein the leaves are arranged sideways and adjacently in the leaf frame for shielding beams being emitted from a radiation source located above the assembly, wherein each leaf is mounted in the leaf frame displaceably in an adjusting direction being oriented perpendicularly related to said beams, and wherein the leaf frame provides a linear guidance for each leaf within the adjusting direction. Additionally, the invention relates to a multi-leaf collimator.

Various embodiments of multi-leaf collimators comprising leaf assemblies each featuring a leaf frame and a plurality of leaves are known in the art. Multi-leaf collimators of such kind are preferably employed for controlling a shape of a high-energy radiation beam emanating from a radiation source and propagating in a direction of propagation. As a matter of course, the leaf frame will usually be located outside the shaped beam.

Multi-leaf collimators are commonly used in treatment devices for oncological radiation therapy. Said collimators delimit high-energy beams, in most cases high energy radiation of a linear accelerator, in such a way that the beams have exactly the same shape as the treatment object. Since such irradiation, e.g. of a tumor, occurs from various directions, it is possible to achieve a great irradiation intensity of the tumor and, at the same time, to stress the surrounding tissue only to a limited extent.

The leaves of the multi-leaf collimator may also be called "shutter blades" or "lamellae". The multi-leaf collimators may also be called contour collimators since due to the positioning of the leaves, contours of treatment objects, for example tumors, can be recreated for each beam application, each of which occurs from a certain solid angle. This is important in order to protect the adjacent healthy tissue to the greatest extent possible. In the case of organs at risk, such as spine or nerves, this is particularly necessary in order to preserve their functional capability.

A general example of a multi-leaf collimator comprising leaf assemblies with a leaf frame and a plurality of leaves is obtainable from U.S. Pat. No. 4,794,629. In such multi-leaf collimators, each leaf must be moved into a certain position. Thus, in most cases, a leaf drive unit is being assigned to each leaf for displacing each leaf within an adjusting direction.

WO 2009/036813 A1 discloses a multi-leaf collimator with rotatory electromechanical motor and operating method. This printed publication discloses a leaf assembly for a multi-leaf collimator and a multi-leaf collimator of the kind mentioned at the beginning of this specification. A plurality of leaves is arranged side-by-side in a leaf frame in displaceable fashion.

However, a major backlash in radiotherapy treatment according to this state of the art is embodied by the occurrence of leakage radiation. In order to enable individual displacement of the various leaves in the adjusting direction, a small gap has to remain between adjacent leaves, inevitably allowing leakage radiation to reach through said gap. Thus, the selected area may not be completely shielded from radiation, resulting in an inexact and even harmful irradiation treatment.

During an irradiation treatment, the irradiation head usually has to be moved into various but defined angles with respect to the target volume, e.g. the tumor. However, with changing positions within one treatment cycle, the alignment of said gaps with respect to the radiation source will vary, again resulting in unwanted and hardly predictable leakage radiation. Also, when the irradiation head is moved in the manner described above, variations in the position of the irradiation head result in changes to the adjusting position of the leaves, because the weight of the leaf units interacting with the slackness of the leaf adjustment within the transmission and/or within the guidance of the leaf displacement will further enable leak radiation to emerge.

In order to diminish the occurrence of leak radiation, it is known in the art to alter the plain design of the leaf surface such that a labyrinth- or meander-like gap (as seen from the top to the bottom of the leaves) between adjacent leaves is attained. Such designs may for instance be implemented by a tongue-and-groove or a step-like design of the leaf surface.

Thus, seen from above, the surface of adjacent leaves may interlock to diminish leak radiation. Various designs being known in this respect like "Elekta", "Siemens" and "Varian" are for instance disclosed in Hariri et al., "Suggesting a new design for multileaf collimator leaves based on Monte Carlo simulation of two commercial systems", J. of Appl. Clinical Medical Physics, Vol. 11, 3 (2010).

However, even when creating a labyrinth-like gap between adjacent leaves, at least a portion of the gap being in alignment with the radiation source may still be permeable by leak radiation.

Also, it has been proposed to incline the entire leaf assembly related to the radiation source in order to misalign said gaps with respect to the radiation beam. However, a remainder of the gap will still be permeable by leak radiation, and, before all, this solution does not work well if the radiation source is not point-shaped.

The invention is therefore based on the objective of relieving at least one of the drawbacks as outlined above.

The invention is additionally based on the objective of designing a leaf assembly for a multi-leaf collimator and a multi-leaf collimator of the kind mentioned at the beginning, respectively, in such a way that the occurrence of leak radiation may be diminished.

This objective is attained in accordance with the invention by the subject-matter disclosed in the independent claims. Preferred embodiments which may be realized in an isolated way or in combination with other preferred embodiments are disclosed subsequently and in the dependent claims.

Thus, in a first major aspect of the present invention, a leaf assembly for a multi-leaf collimator of the kind mentioned at the beginning is designed in such a way that the leaf frame is adapted to allow for lateral movement of the leaves superposing said linear guidance, thus allowing mutual abutting of the leaves.

Therefore, according to the invention, the benefits of a linear leaf guidance for precise mounting and displacement in the adjusting direction may be combined with a substantial reduction or even a complete prevention of leak radiation.

Although the leaf frame provides a linear guidance for each leaf, the linear guidance may be superposed by a lateral leaf movement resulting in a mutual abutting of the leaves, i.e. the sidewise contacting of the surface of adjacent leaves. By way of said mutual abutting, the gap between adjacent leaves may be substantially diminished, and may preferably be eliminated altogether. Thus, an assembly may be implemented which allows leaves to contact adjacent leaves with the entity of their surface when abutting.

The mutual abutting of adjacent leaves by sidewise contacting of the surface of adjacent leaves is regarded as yielding a superior shielding of leakage radiation compared to aforementioned techniques. In particular, by way of a possible elimination of the gap between adjacent leaves, no gap or gap portion will remain to allow the unwanted propagation of leak radiation.

The term "leaf frame" as used herein generally relates to any means for mounting leaves sideways and adjacently (i.e. side-by-side) in the path of a radiation beam. Also, it is noted that said leaf frame does not necessarily enclose or surround the leaf completely. Thus, the leaf frame may also be designed as a rack, rail or any other suitable member being adapted to mount a plurality of leaves. The leaf frame will usually be positioned outside the shaped radiation beam.

The term "linear guidance" as used herein refers both to a technical means and to a technical effect achieved by appropriate means which properly impede the leaf from unwantedly deviating from the axis represented by the adjusting direction if not deliberately initiated by a user or automatically in order to superpose said linear guidance.

In a first optional and preferred embodiment of the leaf assembly according to the invention, the leaves exhibit a conical cross-sectional area. Said cross-sectional area should be understood as the surface which would be generated by cutting the leaf in a vertical line, i.e. in the direction of the beam propagation. According to this embodiment, adjacent leaves may advantageously be abutted by shifting or moving adjacent leaves in an upward direction. Also, due to said conical shape, the leaves may shield the radiation in a fanshaped fashion.

In a further optional and preferred embodiment, the lateral movement allowed for by the leaf frame is constitutable as an increment of an inclined upward movement of the leaves. This embodiment may preferably be implemented in addition to the above-mentioned embodiment, i.e. designing the leaves with a conical cross-sectional area as defined above. According to this aspect of the invention, an inclined upward movement of—preferably conical—leaves may result in an abutting of adjacent leaves which may be characterized as a mutual jamming of the leaves, pressing adjacent leaf surfaces onto each other and thus eliminating any gaps between the leaves completely. In particular, the upward movement may be inclined towards the usual position of the radiation source in relation to the leaf frame, thus being inclined towards a usual beam direction.

Optionally, in a further embodiment of the leaf assembly according to the invention, the linear guidance is provided by grooves in the leaf frame which extend longitudinally in the adjusting direction. In other words, such grooves will extend perpendicularly related to a beam emitted from a radiation source being located in the usual position, i.e. above the leaf assembly.

Preferably, in a further embodiment, the depth of said grooves allows for an upward movement of the leaves. Thus, the grooves may be designed deeper than it would be necessary for merely providing linear guidance for the leaves. By designing the grooves with a depth as defined here, the grooves will enable the leaves to be shifted upwards but still providing linear guidance in the adjusting direction and perpendicularly to the direction of shifting. Further preferably, the grooves may be machined to extend into the frame as being tilted against the vertical line and/or a beam emanating from a radiation source positioned above the assembly. Thus, the design of the grooves will automatically promote an abutting or even mutual jamming of adjacent leaves if the leaves are subject to an upward movement.

Hence, in a further optional embodiment, said grooves are tilted with respect to beams being emitted from a radiation source located above the assembly.

Alternatively or additionally, according to a further preferred embodiment, laterally flexible elements are arranged between the leaf frame and the leaves. In particular, said flexible elements may be attached to the upper end and/or the lower end of a leaf and, from there, extend into a suitably designed recess within the leaf frame. Preferably, said recess may be a groove according to any one of the above embodiments featuring a groove in the leaf frame. Preferably, the leaves are displaceable in the adjusting direction gliding with respect to the flexible elements which are attached to the leaf frame. According to this embodiment, laterally flexible elements provide for the leaves being shiftable in a lateral direction in order to abut with each other, while said flexible elements still pass over the necessary linear guidance from the leaf frame to the leaves within the adjusting direction. The lateral movement of the leaves may be induced by a suitable external clamping or pressing force operating against the reset force of the laterally flexible elements. The person skilled in the art is aware of various technical means which are suitable to effect said clamping or pressing force directed perpendicularly to both the adjusting direction and the beam direction.

In a further preferred option related to the last-mentioned embodiment, the laterally flexible elements comprise spring steel elements.

In yet a further embodiment of the leaf assembly according to the invention, the linear guidance provided by the leaf frame is adapted to interact with one side of the leaves, whereas the opposite side of the leaves is tiltable, allowing mutual abutting of the leaves. Hence, it is proposed that the leaf frame be designed to provide linear guidance for the leaf predominantly or exclusively on one side of the leaf, in particular the lower side of the leaf, whereas the other side, in particular the upper side, may be tiltable at least to an extent which allows abutting or even mutual jamming of adjacent leaves. According to this embodiment, the leaves may easily be adjusted within the adjusting direction while not being abutted to each other. While not being abutted, the leaves will not mutually exert considerable friction forces which could obstruct the linear adjusting to select the area to be shielded from radiation beams. However, once the linear adjusting of the leaves is accomplished, the leaves may be tilted against each other, resulting in a preferable mutual abutting to prevent the propagation of leakage radiation. Preferably, the leaves may be tiltable towards the usual position of a radiation source, i.e. above a leaf assembly and centered related to the assembly. The person skilled in the art will choose appropriate technical means in order to tilt the leaves, i.e. applying a suitable clamping or pressing force directed perpendicularly to both the adjusting direction and the beam direction.

Further optionally, related to the above embodiment, the linear guidance may comprise rounded grooves in the leaf frame which extend longitudinally in the adjusting direction. The rounded grooves facilitate an enhanced tiltability of the leaves and also improve the quality of the linear guidance provided by the leaf frame. With respect to this embodiment, the non-tiltable side, in particular the lower side, of the leaves should feature a corresponding, inverse curvature to properly fit the rounded grooves.

In a second major aspect of the invention, a multi-leaf collimator is disclosed, wherein the multi-leaf collimator comprises two leaf assemblies according to the invention, wherein the assemblies are arranged to face each other within the adjusting direction.

Relating to the essence and features of the multi-leaf collimator according to the invention, reference is at first made to all previous paragraphs of this specification. In other words, the essence and benefits of the multi-leaf collimator according to the invention will already become manifest from the previous paragraphs describing aspects of the leaf assembly. Also, it is obvious that within the multi-leaf collimator according to the invention, any embodiment or any combination of aspects of the leaf assembly according to the invention as described in the previous parts of this specification may be employed. When being employed within the multi-leaf collimator according to the invention, it is understood that the leaf assembly according to the invention and/or further aspects of the leaf assembly according to the optional embodiments as explained above, also aspects being combined, will yield the advantageous effects as described above also with relation to the multi-leaf collimator.

Summarizing, the following embodiments are preferred embodiments of the present invention:

EMBODIMENT 1

A leaf assembly for a multi-leaf collimator, comprising a leaf frame and a plurality of leaves for shielding beams from a selected area, wherein the leaves are arranged sideways and adjacently in the leaf frame for shielding beams being emitted from a radiation source located above the assembly, wherein each leaf is mounted in the leaf frame displaceably in an adjusting direction being oriented perpendicularly related to said beams, and wherein the leaf frame provides a linear guidance for each leaf within the adjusting direction, characterized in that the leaf frame is adapted to allow for lateral movement of the leaves superposing said linear guidance, thus allowing mutual abutting of the leaves.

EMBODIMENT 2

The leaf assembly according to the preceding embodiment, characterized in that the leaves exhibit a conical cross-sectional area.

EMBODIMENT 3

The leaf assembly according to any one of the preceding embodiments, characterized in that the lateral movement allowed for by the leaf frame is constitutable as an increment of an inclined upward movement of the leaves.

EMBODIMENT 4

The leaf assembly according to any one of the preceding embodiments, characterized in that the linear guidance is provided by grooves in the leaf frame which extend longitudinally in the adjusting direction.

EMBODIMENT 5

The leaf assembly according to the preceding embodiment, characterized in that the depth of the grooves allows for an upward movement of the leaves.

EMBODIMENT 6

The leaf assembly according to any one of embodiments 4 or 5, characterized in that the grooves are tilted with respect to beams being emitted from a radiation source located above the assembly.

EMBODIMENT 7

The leaf assembly according to any one of the preceding embodiments, characterized in that laterally flexible elements are arranged between the leaf frame and the leaves.

EMBODIMENT 8

The leaf assembly according to the preceding embodiment, characterized in that the laterally flexible elements comprise spring steel elements.

EMBODIMENT 9

The leaf assembly according to any one of the preceding embodiments, characterized in that the linear guidance provided by the leaf frame is adapted to interact with one side of the leaves, whereas the opposite side of the leaves is tiltable, allowing mutual abutting of the leaves.

EMBODIMENT 10

The leaf assembly according to the preceding embodiment, characterized in that the linear guidance comprises rounded grooves in the leaf frame which extend longitudinally in the adjusting direction.

EMBODIMENT 11

A multi-leaf collimator, characterized in that the collimator comprises two leaf assemblies according to any one of the preceding embodiments, wherein the assemblies are arranged to face each other within the adjusting direction.

In the following, the invention will further be explained by way of both schematic and exemplary drawings. In the figures, identical reference numbers refer to identical components or components having the same or similar functions. Thus, such components and referring reference numbers might not be explained with regard to each figure, and explanations given on the occasion of preceding figures are referred to in such cases. In the figures, aspects of the leaf assembly and also aspects of the multi-leaf collimator according to the invention will be explained referring to preferred embodiments. While explaining aspects of the leaf assembly according to the invention, reference will also be made to aspects of the multi-leaf collimator according to the invention. The exemplary embodiments related to in the figures and the referring explanations are merely given for illustrative purposes, and the invention is not restricted to these embodiments.

Shown are in

Figure 2:
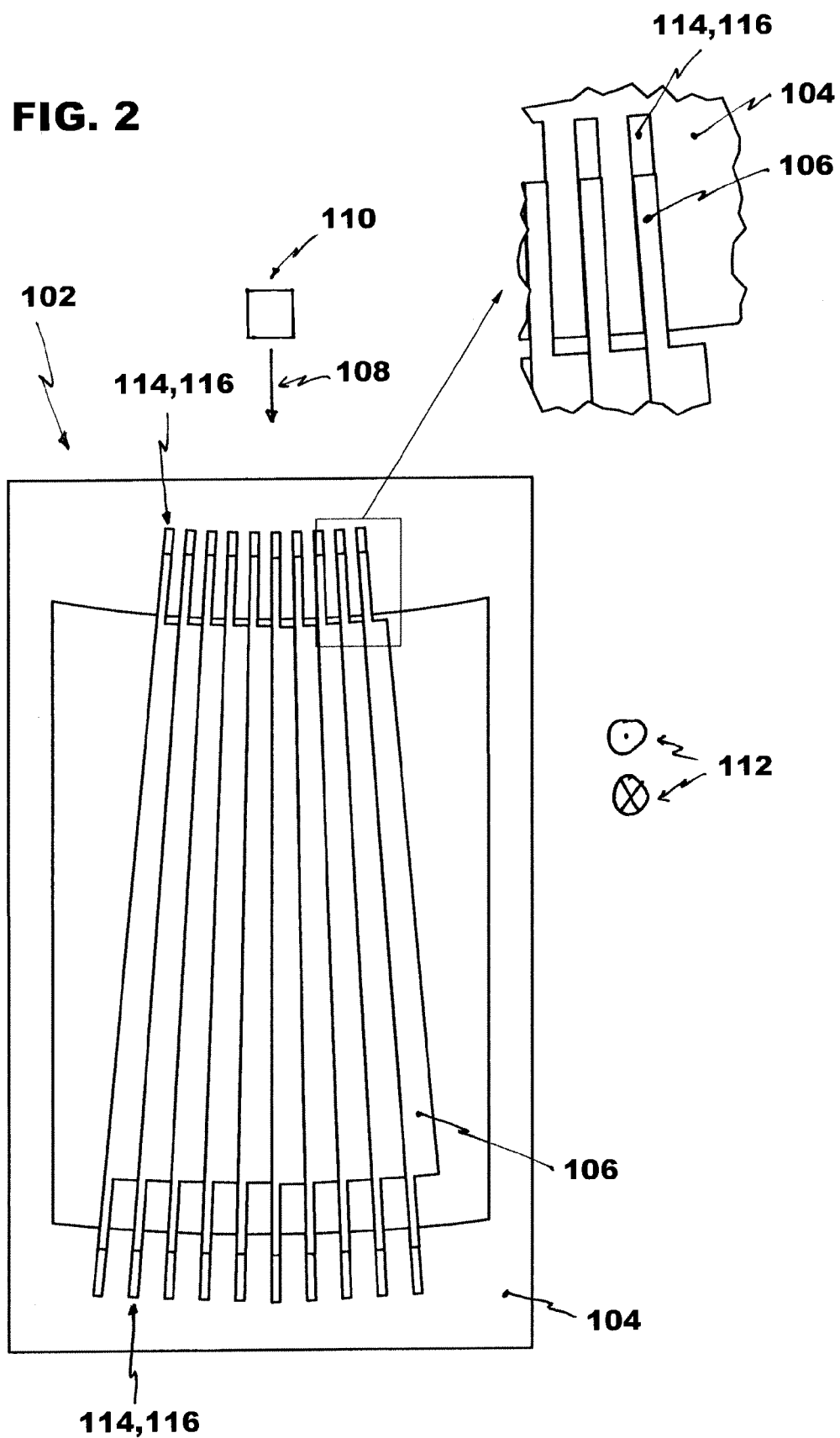
Figure 3:
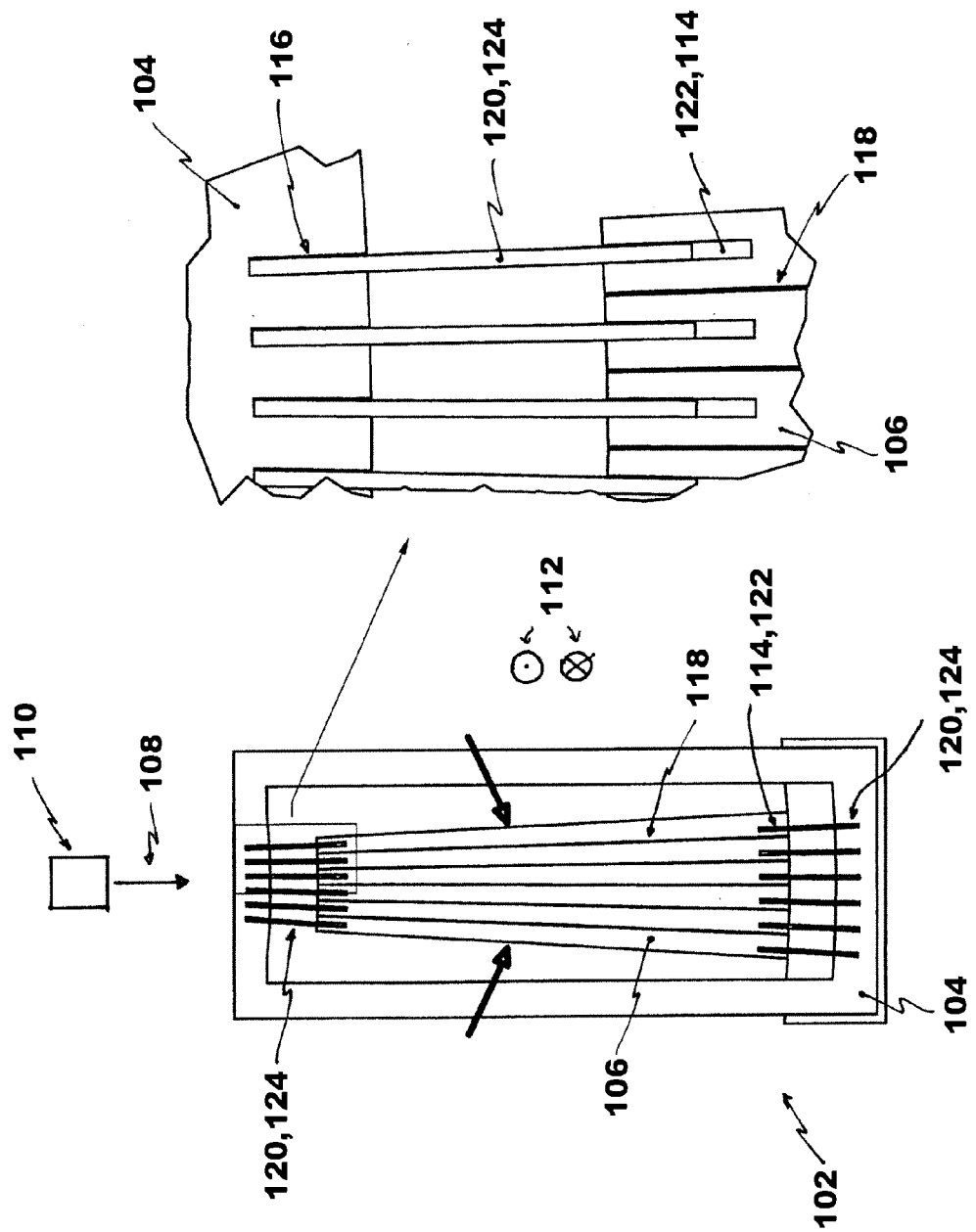
Figure 4:
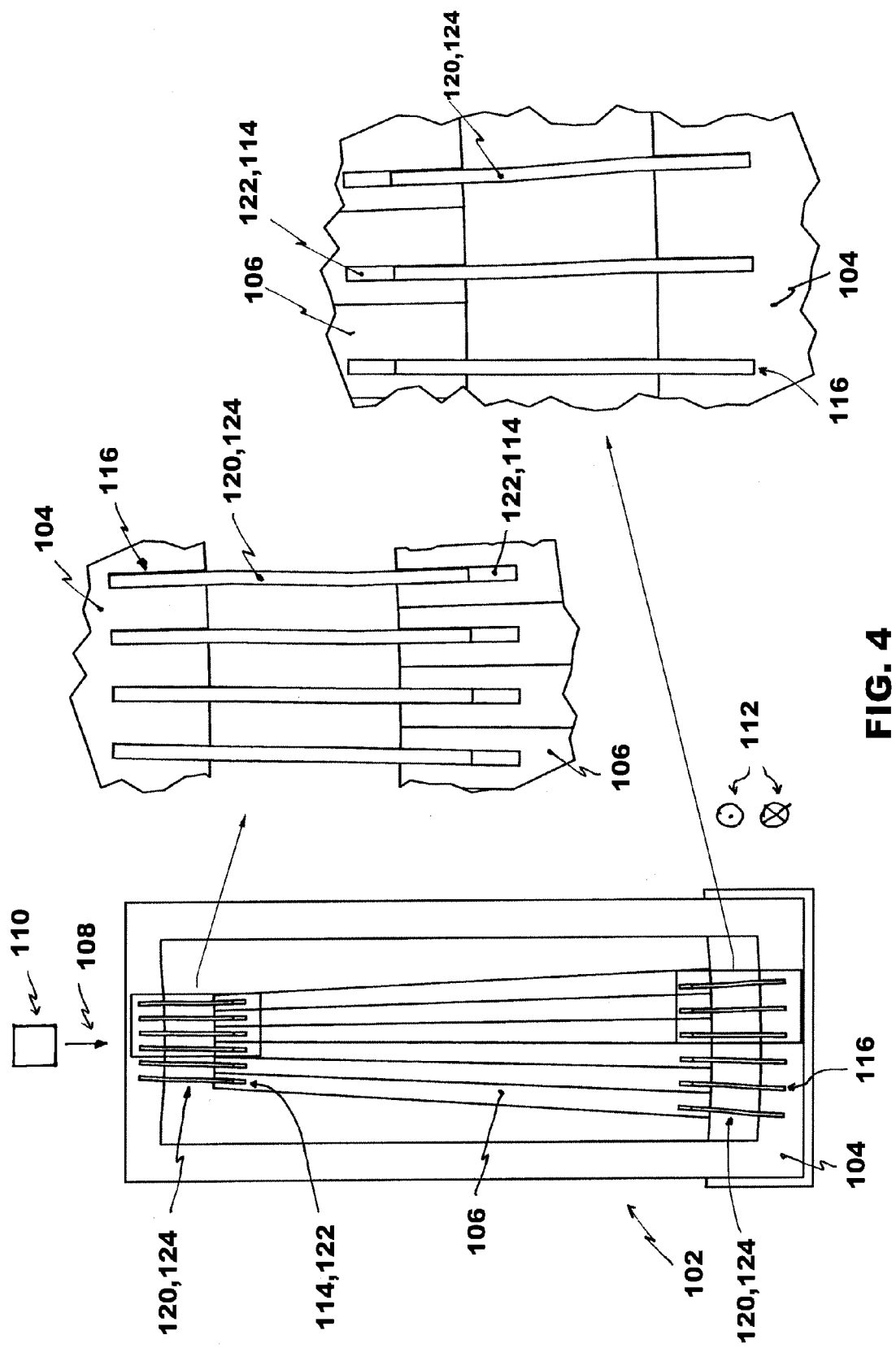
Figure 5:
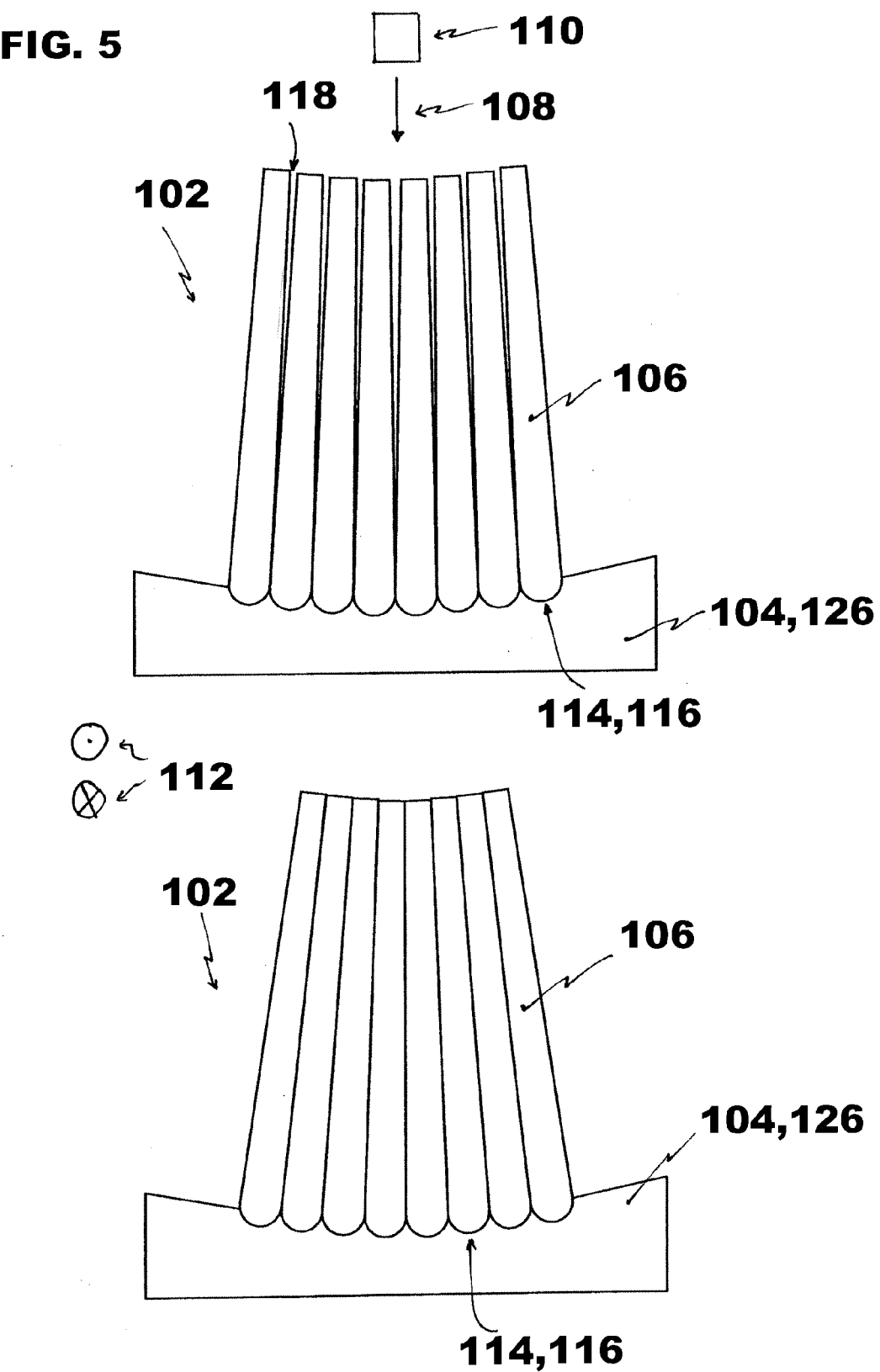
Figure 6:
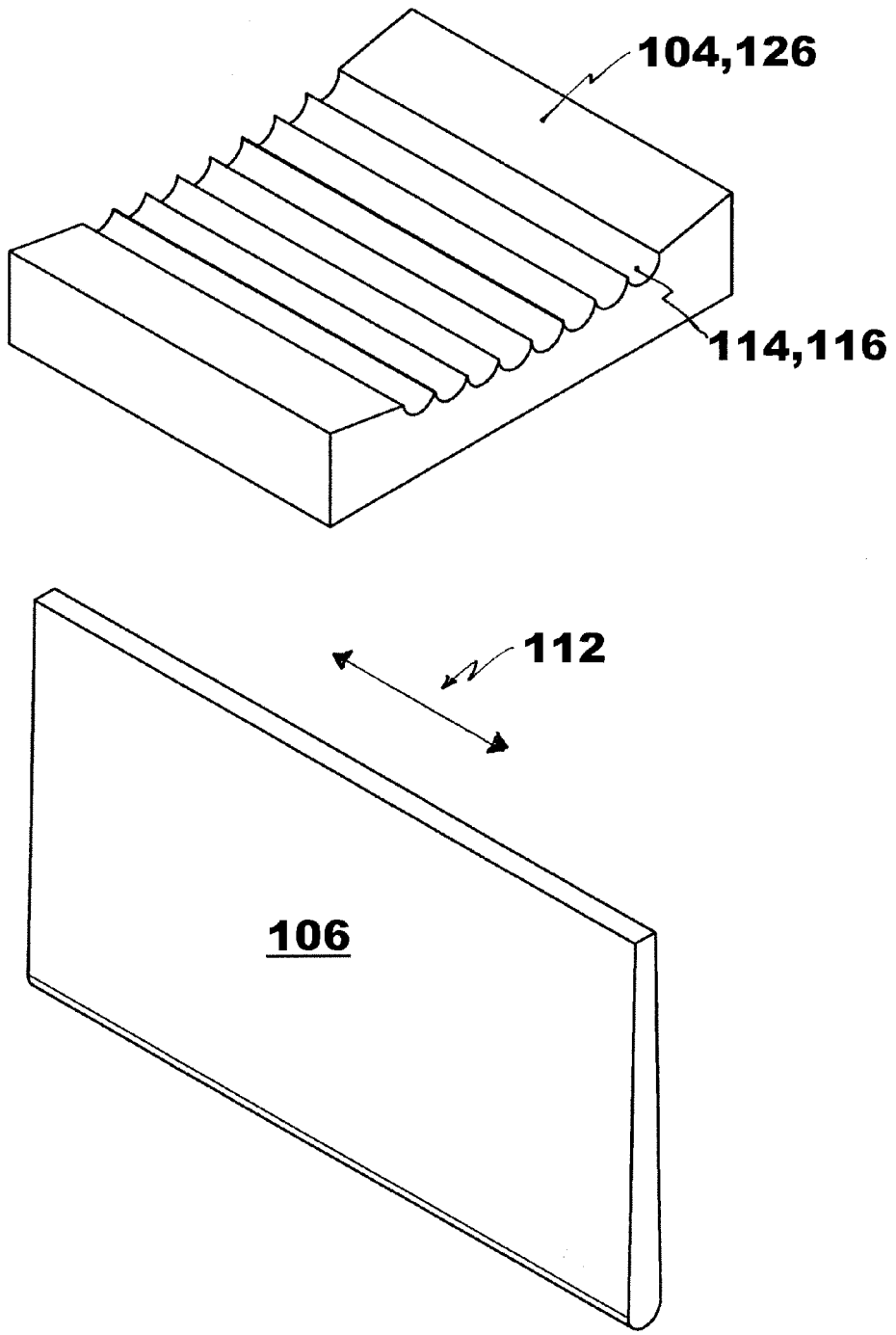

FIG. 1 in a sectional side view with two magnified details a first exemplary embodiment of the leaf assembly according to the invention, FIG. 2 the leaf assembly according to the embodiment shown in FIG. 1, however now with abutted leaves, FIG. 3 in a sectional side view with a magnified detail a second exemplary embodiment of the leaf assembly according to the invention, FIG. 4 the leaf assembly according to the embodiment shown in FIG. 3, however now with abutted leaves, FIG. 5 in a predominantly schematic side view a third exemplary embodiment of the leaf assembly according to the invention, shown both with non-abutted leaves (top) and abutted leaves (bottom), and FIG. 6 in a perspective view the leaf frame (top) and one leaf (bottom) of the leaf assembly according to the embodiment shown in FIG. 5.

FIG. 1 discloses in a sectional and predominantly schematical side view a first exemplary and preferred embodiment of the leaf assembly 102 according to the invention. Also, two magnified details of the assembly 102 are shown which relate to the upper and the lower portion of the leaf assembly 102, respectively. The leaf assembly 102 is adapted to be arranged within a multi-leaf collimator (not shown) in a usual way which is familiar to the person skilled in the art.

The leaf assembly 102 comprises a leaf frame 104 and a plurality of leaves 106 for shielding beams 108 from a selected area, wherein the leaves 106 are arranged sideways and adjacently in the leaf frame 104 for shielding beams 108 being emitted from a radiation source 110 located above the assembly. The radiation source 110 is schematically shown for reasons of clarity and understanding of the invention, but is however not comprised by the leaf assembly 102 according to the invention.

Each leaf 106 is mounted in the leaf frame 104 displaceably in an adjusting direction 112 being oriented perpendicularly related to said beams 108. The adjusting direction 112 is illustrated by two arrows facing outside and inside the plane of projection, respectively.

It is noted that according to this embodiment, each leaf 106 exhibits a conical cross-sectional area as can be seen in this cross-sectional illustration. The conical shaping facilitates a fan-like shielding of a beam 108, and also promotes mutual abutting of the leaves 106 (see explanation below).

Further, the leaf frame 104 provides a linear guidance 114 for each leaf 106 within the adjusting direction 112. Here, the linear guidance 114 is provided by grooves 116 in the leaf frame 104 which extend longitudinally in the adjusting direction 112.

According to the invention, the leaf frame 104 is adapted to allow for lateral movement of the leaves 106 superposing the linear guidance 114, thus allowing mutual abutting of the leaves 106 to prevent leak radiation emanating from the radiation source 110 to permeate the leaf assembly 102 within the selected area which should be shielded from beams 108.

For this purpose, the embodiment of the leaf assembly 102 according to FIG. 1 comprises grooves 116 in the leaf frame 104 which are deep enough to allow for an upward movement of the leaves 106. Also, the grooves 116 are tilted with respect to the vertical line and also with respect to beams 108 being emitted from the radiation source 110 located above the assembly 102.

Consequently, the lateral movement of the leaves 106 allowed for by the leaf frame 104 is constitutable as an increment of an inclined upward movement of the leaves 106.

It is noted that according to FIG. 1, the leaf assembly 102 is illustrated with the leaves 106 not yet shifted upwardly, i.e. the assembly 102 is shown in the initial position. In particular the two magnified details also shown in FIG. 1 illustrate that the lower portion of the leaves 106 extend to the bottom of the grooves 116 in the lower part of the leaf frame 104, whereas there remains a space between the upper portion of the leaves 106 and the top of the grooves 116 in the upper part of the leaf frame 104 which allows an upward movement of the leaves 106.

Also, according to FIG. 1, there exists a small gap 118 between adjacent leaves 106, allowing a trouble-free individual adjusting of each leaf 106.

FIG. 2 illustrates the leaf assembly 102 according to the embodiment shown in FIG. 1, however now with abutted leaves 106. The leaves 106 have been moved or shifted upwardly, being guided by and seated in the grooves 116. Comparing to the situation illustrated in FIG. 1, it is noted that the lower portion of the leaves 106 no longer extends to the bottom of the grooves 116 in the lower part of the leaf frame 104, and the space remaining between the upper portion of the leaves 106 and the top of the grooves 116 in the upper part of the leaf frame 104 has been reduced. The upward movement of the leaves 106 is performable until the leaves 106 will abut mutually due to the lateral movement of the leaves 106 which is automatically induced by shifting the leaves 106 upwardly. Here, the leaves 106 may be moved upwardly not only until abutting, but even until being jammed against each other.

It becomes apparent that the leaves 106 being abutted or even jammed as shown in FIG. 2 do no longer exhibit a gap between adjacent leaves 106, thus the occurrence of leakage radiation may be suppressed completely.

For reasons of clarity, no technical means or member is illustrated in FIGS. 1 and 2 to move the leaves 106 upwardly. The person skilled in the art will be aware of appropriate manual, electrical or motor-driven means and make an unconstrained selection without having to depart from the invention.

FIG. 3 shows a sectional and predominantly schematical side view of a second exemplary and preferred embodiment of the leaf assembly 102 according to the invention. Also, a magnified detail of the upper portion of some leaves 106 is illustrated.

According to this embodiment, laterally flexible elements 120 are arranged between the leaf frame 104 and the leaves 106. It is particularly well obtainable from the magnification on the right side of this figure that one end of each laterally flexible element 120 is attached to a groove 116 in the leaf frame 104, whereas the other end is slidably arranged in a suitable recess 122 in the leaf 106. Preferably, the recess 122 exhibits a groove-like shaping. The laterally flexible elements 120 exhibit a plate-like shape. Also, here the laterally flexible elements 120 comprise spring steel elements 124 for providing an adequate lateral reset force.

The schematically sketched arrows on both sides of the leaf frame 102 on the left side of FIG. 3 illustrate the mode of operation concerning this embodiment. In order to effect a lateral movement of the leaves 106 superposing the linear guidance 114, a clamping or pressing force may be applied to the adjacently mounted leaves 106. Such a force will appropriately deflect the laterally flexible elements 120, thus allowing mutual abutting of the leaves 106. Said abutting is not yet shown according to FIG. 3, as it is obtainable particularly from the magnification that the spring steel elements 124 are not yet deflected. Also, between adjacent leaves 106, gaps 118 do still exist.

FIG. 4 illustrates the leaf assembly 102 according to the embodiment shown in FIG. 3, however now with abutted leaves 106. A pressing or clamping force has been laterally applied to the leaves 106, or, with other words, the leaves 106 have been squeezed or pressed against each other laterally.

Comparing to the situation illustrated in FIG. 3, it is noted that the laterally flexible elements 120, i.e. the spring steel elements 124, are visibly deflected owing to the clamping force applied to the multitude of adjacent leaves 106. The deflection of the laterally flexible elements 120 is particularly well detectable from the two magnifications of details provided on the right side of FIG. 4.

It becomes apparent that the leaves 106 being abutted as shown in FIG. 4 do no longer exhibit a gap between adjacent leaves 106, thus the occurrence of leakage radiation may be suppressed completely.

For reasons of clarity, no technical means or member is illustrated in FIGS. 3 and 4 serving to apply a clamping or pressing force as outlined above to the stack of adjacent leaves 106. The person skilled in the art will be aware of appropriate manual, electrical or motor-driven means and make an unconstrained selection without having to depart from the invention.

FIG. 5 shows a predominantly schematic side view of a third exemplary and preferred embodiment of the leaf assembly 102 according to the invention. This figure comprises two illustrations of said embodiment, the first one showing the leaf assembly 102 with non-abutted leaves 106 (top of FIG. 5), and the second one showing said assembly 102 with abutted leaves 106 (bottom of FIG. 5).

According to this embodiment of the leaf assembly 102, the leaf frame 104 is designed as a rack 126 or rail which extends longitudinally in the adjusting direction 112. Additionally, the linear guidance 114 provided by the leaf frame 104 is adapted to interact with one side, i.e. the bottom side of the leaves 106, whereas the opposite side, i.e. the top side of the leaves 106 is tiltable, allowing mutual abutting of the leaves 106.

For this purpose, a rather simple setup is proposed, wherein the leaf frame 104, i.e. the rack 126 comprises rounded grooves 116 which extend longitudinally in the adjusting direction 112. Also, the lower end of the leaves 106 are designed with a complementary round shaping, snugly fitting the grooves 116. The pairing of said lower end of the leaves 106 with the rounded grooves 116 provides for an effective tiltability of the leaves 106 with relation to the linear guidance 114.

The top of FIG. 5 shows the leaf assembly 102 with non-tilted and non-abutted leaves 106. In this situation, gaps 118 do exist between adjacent leaves 106, and each leaf 106 may be individually displaced and adjusted in the adjusting direction 112 excellently owing to low or even no friction occurring with respect to other leaves 106.

The bottom of FIG. 5 illustrates the leaf assembly 102 now with abutted leaves 106. A pressing or clamping force has been laterally applied to the leaves 106, or, with other words, the leaves 106 have been squeezed or pressed against each other laterally.

Comparing to the situation illustrated in the top portion of FIG. 5, it is noted that the leaves 106 being abutted as shown in the bottom sketch of FIG. 5 do no longer exhibit a gap between adjacent leaves 106, thus the occurrence of leakage radiation may be suppressed completely.

For reasons of clarity, no technical means or member is illustrated in FIG. 5 serving to apply a clamping or pressing force as outlined above to the stack of adjacent leaves 106. The person skilled in the art will be aware of appropriate manual, electrical or motor-driven means and make an unconstrained selection without having to depart from the invention.

FIG. 6 provides an additional perspective view of the leaf frame 102, i.e. the rack 126 (top of FIG. 6) and one exemplary leaf 106 (bottom of FIG. 6) of the leaf assembly 102 according to the embodiment shown in FIG. 5. Here, the rounded grooves 116 extending longitudinally in the rack 126 within the adjusting direction 112 are well visible. Further, it is noted that the rack 126 itself exhibits a concave shaping (as seen from above) to promote abutting of the leaves 106.

Also, the shaping of the complementary leaf 106 becomes apparent, with the round design of the lower end of the leaf 106 providing an excellent tiltability with relation to the rack 126.

LIST OF REFERENCE SYMBOLS 102 leaf assembly
104 leaf frame
106 leaf
108 beam (radiation)
110 radiation source
112 adjusting direction
114 linear guidance
116 groove
118 gap (between adjacent leaves)
120 laterally flexible element
122 recess (leaf)
124 spring steel element
126 rack (leaf frame)

The invention claimed is:

1. A leaf assembly for a multi-leaf collimator, comprising a leaf frame and a plurality of leaves for shielding beams from a selected area,
   wherein the leaves are arranged sideways and adjacently in the leaf frame for shielding beams being emitted from a radiation source located above the assembly,
   wherein each leaf is mounted in the leaf frame displaceably in an adjusting direction being oriented perpendicularly related to the beams,
   wherein the leaf frame provides a linear guidance for each leaf within the adjusting direction, and
   wherein the leaf frame is configured to allow for lateral movement of the leaves superposing the linear guidance, thereby allowing mutual abutting of the leaves.

2. The leaf assembly according to claim 1, wherein the leaves have a conical cross-sectional area.

3. The leaf assembly according to claim 1, wherein the lateral movement allowed for by the leaf frame comprises an increment of an inclined upward movement of the leaves.

4. The leaf assembly according to claim 1, wherein the linear guidance is provided by grooves in the leaf frame which extend longitudinally in the adjusting direction.

5. The leaf assembly according to claim 4, wherein a depth of the grooves allows for an upward movement of the leaves.

6. The leaf assembly according to claim 4, wherein the grooves are tilted with respect to the beams emitted from the radiation source located above the assembly.

7. The leaf assembly according to claim 1, further comprising laterally flexible elements arranged between the leaf frame and the leaves.

8. The leaf assembly according to claim 7, wherein the laterally flexible elements comprise spring steel elements.

9. The leaf assembly according to claim 1, wherein the linear guidance provided by the leaf frame is configured to interact with one side of the leaves, whereas the opposite side of the leaves is tiltable, allowing mutual abutting of the leaves.

10. The leaf assembly according to claim 9, wherein the linear guidance comprises rounded grooves in the leaf frame which extend longitudinally in the adjusting direction.

11. A multi-leaf collimator, comprising two leaf assemblies according to claim 1, wherein the two leaf assemblies are arranged to face each other within the adjusting direction.

* * * * *